(12) United States Patent
Aiba

(10) Patent No.: US 7,597,006 B2
(45) Date of Patent: Oct. 6, 2009

(54) METHOD OF EVALUATING ADHESIVENESS OF MEMBER

(75) Inventor: Toshiaki Aiba, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 11/147,179

(22) Filed: Jun. 8, 2005

(65) Prior Publication Data

US 2005/0274198 A1    Dec. 15, 2005

(30) Foreign Application Priority Data

Jun. 9, 2004   (JP) .............................. 2004-171305
May 17, 2005   (JP) .............................. 2005-144069

(51) Int. Cl.
   *G01N 3/08* (2006.01)
(52) U.S. Cl. ...................................... 73/827
(58) Field of Classification Search ............... 73/827
   See application file for complete search history.

(56) References Cited

U.S. PATENT DOCUMENTS

| | | | | |
|---|---|---|---|---|
| 3,605,486 A | * | 9/1971 | Anderholm et al. | 73/788 |
| 3,634,930 A | * | 1/1972 | Cranston | 438/15 |
| 4,194,392 A | * | 3/1980 | Lombard et al. | 73/150 A |
| 4,232,559 A | * | 11/1980 | Favre et al. | 73/827 |
| 5,201,230 A | * | 4/1993 | Sakakibara | 73/827 |
| 5,270,552 A | | 12/1993 | Ohnishi et al. | 250/307 |
| 5,838,446 A | * | 11/1998 | Meth et al. | 356/632 |
| 5,841,034 A | * | 11/1998 | Ball | 73/800 |
| 6,188,068 B1 | * | 2/2001 | Shaapur et al. | 250/307 |
| 6,308,560 B1 | * | 10/2001 | Bracht | 73/150 R |
| 6,455,152 B1 | * | 9/2002 | DiZio et al. | 428/345 |
| 6,532,805 B1 | | 3/2003 | Kokawa et al. | 73/105 |
| 6,538,254 B1 | | 3/2003 | Tomimatsu et al. | 250/442.11 |
| 6,555,175 B2 | * | 4/2003 | Johnson | 427/399 |
| 6,813,958 B2 | * | 11/2004 | Crosby et al. | 73/800 |
| 7,176,458 B2 | * | 2/2007 | Tomimatsu et al. | 250/306 |

FOREIGN PATENT DOCUMENTS

| | | |
|---|---|---|
| JP | 52-29792 A | 3/1977 |
| JP | 3-17534 A | 1/1991 |
| JP | 3-61556 | 6/1991 |
| JP | 4-250339 | 9/1992 |
| JP | 5-52721 A | 3/1993 |
| JP | 6-167441 | 6/1994 |
| JP | 9-184794 | 7/1997 |
| JP | 11-258131 | 9/1999 |
| JP | 2002-5817 | 1/2002 |
| WO | WO 99/05506 A1 | 2/1999 |

* cited by examiner

*Primary Examiner*—Lisa M Caputo
*Assistant Examiner*—Octavia Davis
(74) *Attorney, Agent, or Firm*—Fitzpatrick, Cella, Harper & Scinto

(57) ABSTRACT

An adhesiveness evaluation method that can be used to accurately evaluate the adhesiveness of a selected specific microspot of a specimen 1 of a small size. A part to be measured 5 is produced by isolating it from a surrounding part 4 and fixing it to a μ-probe 6, which is a support member. Then, the pulling force is applied to the part to be measured 5 using the μ-probe 6, which is the support member and which is fixed to it, to evaluate the adhesiveness of the part to be measured 5.

7 Claims, 2 Drawing Sheets

METHOD OF EVALUATING ADHESIVENESS OF MEMBER

BACKGROUND OF THE INVENTION

1. Field of the Invention

This invention relates to a method of evaluating the adhesiveness of a member. More particularly, the present invention relates to an adhesiveness evaluation method that can suitably be used for evaluating the adhesiveness of a thin film in a micro-region.

2. Related Background Art

Known adhesiveness evaluation methods (e.g., a method of evaluating the adhesiveness of a thin film relative to a substrate on which the film is formed, for example) include the pulling/peeling test, the scratching test and the pressure mark test.

With the cross-cut adhesion test, which is a type of pulling/peeling test, the thin film formed on a substrate is cut to produce a checker pattern and a sticky tape is applied to the surface of the thin film. Subsequently, the sticky tape is peeled off and the number of small squares of thin film that are peeled off from the substrate with the sticky tape is counted to evaluate the adhesiveness of the thin film.

With the scratch test, a very hard needle (stylus) is vertically pressed against the thin film formed on a substrate and then driven to move in a horizontal direction with a load being applied to the stylus in order to scratch the thin film. Then, the load that produces a scratch on the thin film is observed to evaluate the adhesiveness of the thin film.

With the pressure mark test, a load is applied to the surface of the thin film formed on a substrate by means of a micro Vickers hardness meter and then gradually raised so as to evaluate the adhesiveness of the thin film by observing the peeled condition of the thin film produced around the pressure mark on the thin film.

Japanese Patent Application Laid-Open No. 2002-005817 describes a method for evaluating the adhesiveness of a thin film applied and adhered to a substrate by winding a specimen consisting of a substrate and an applied thin film around a part of the test roller having a predetermined diameter and forcing it to bend in order to see the peeled condition of the applied film and evaluate the adhesiveness of the applied film relative to the substrate.

As described above, known adhesiveness evaluation methods have been developed on an assumption of using a macro-size specimen as an object of measurement.

Meanwhile, with the advancement of film-forming techniques and micro-machining techniques in recent years, there has arisen a demand for evaluating the physical properties of a micro-part of a specific spot of a small specimen, which may typically be any of various devices or micro-machines.

The physical properties of a specimen to be evaluated typically include the morphology, the crystallinity, the defects, the impurities and the component elements of the specimen. In certain cases, the adhesiveness of the specimen is also one of the basic parameters to be evaluated.

For instance, the durability and the reliability of a device comprising a thin film showing a poor adhesiveness may be low. In other words, there are many products whose quality is improved when the adhesiveness of the products is improved.

However, a micro-size specimen, which may be any of various devices or micro-machines, more often than not has a complex structure within a micro-part thereof. It means that the adhesiveness can vary within the micro-part. Hence, a specific spot of a micro-part of the specimen may have to be selected and evaluated for adhesiveness.

On the other hand, known adhesiveness evaluation methods have been developed on an assumption of using a macro-size specimen as the object of measurement, as pointed out above. Hence, it is not possible to select a specific spot (of the order of magnitude of nanometers to micrometers) of a micro-part and evaluate the adhesiveness of the spot using any of the known adhesiveness evaluation methods.

Attempts have been made to prepare a sham specimen (for example, a plain thin film formed on a substrate) and evaluate the adhesiveness of the sham specimen by means of a known adhesiveness evaluation method in order to replace an adhesiveness evaluation test of a specific spot of a micro-part of a comparable real specimen (which may be any of various devices or micro-machines). However, in many cases, an adhesiveness evaluation test using such a sham specimen is not equivalent to an adhesiveness evaluation test conducted on a specific spot of a micro-part of a real specimen because the sham specimen and the real specimen do not necessarily represent the same condition.

SUMMARY OF THE INVENTION

In view of the above-identified circumstances, it is therefore an object of the present invention to provide an adhesiveness evaluation method that can accurately evaluate the adhesiveness of a selected specific micro-spot (e.g., of the order of magnitude of nanometers to micrometers) of a specimen.

Another object of the present invention is to provide a method and an apparatus for evaluating the adhesiveness of a member that can facilitate the operation of isolating the part to be measured, suppressing the damage, if any, of the part to be measured and the support member of the part during the isolating operation so as to minimize the adverse effect of the damage on the adhesiveness evaluation.

Still another object of the present invention is to provide a method and an apparatus for highly accurately evaluating the adhesiveness of a member that can suppress the damage of the part to be measured and intensify the fixing strength of the support member of the part.

In an aspect of the present invention, there is provided a method of evaluating the adhesiveness of a member comprising at least:

an isolation step of isolating the part to be measured of a second member arranged on a first member from a surrounding part;

a fixation step of fixing a support member to the part of the second member to be measured after the isolation step;

an evaluation step of applying a pulling force to the part of the second member to be measured by way of the support member and evaluating the adhesiveness of the part of the second member to be measured to the first member.

In another aspect of the present invention, there is provided a method of evaluating the adhesiveness of a member comprising at least:

a step of arranging a support member to the part to be measured of a second member arranged on a first member;

a step of depositing a substance on the part of the second member to be measured carrying the support member arranged thereto and fixing the support member to the part of the second member to be measured; and a step of applying a pulling force to the part of the second member to be measured by way of the support member and evaluating the adhesiveness of the part of the second member to be measured to the first member.

Preferably, the isolation step is conducted by using an ion beam, an electron beam or a light beam.

Preferably, the fixing step is conducted by depositing a substance and fixing the support member to the part to be measured of the second member.

Preferably, the fixing step includes irradiation of one or more than one of an ion beam, an electron beam or a light beam in a gas atmosphere for forming a deposit of a substance.

Preferably, the evaluation step includes a step of pulling the support member or moving a stage holding the specimen.

DESCRIPTION OF THE PREFERRED EMBODIMENTS

Figure 1A:
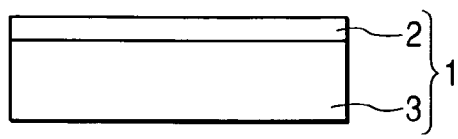
FIGS. 1A, 1B, 1C, 1D, 1E and 1F are schematic cross-sectional views of an arrangement for the first embodiment of an adhesiveness evaluation method according to the invention.

Now, the present invention will be described by referring to the accompanying drawings that illustrate the best mode for carrying out the invention. While a substrate and a thin film are used respectively as the first member and the second member in the following description for the purpose of convenience, the present invention is by no means limited thereto.

FIGS. 1A through 1F are schematic cross-sectional views of an arrangement for the first embodiment of an adhesiveness evaluation method according to the invention.

Referring to FIGS. 1A through 1F, 1 denotes a specimen comprising a first member and a second member, 2 and 3 respectively denote the second member, which is a thin film, and the first member, which is a substrate, and 4 and 5 respectively denote a surrounding part and the part to be measured that is isolated from the surrounding part 4, while 6 and 7 respectively denote a μ-probe that is a support member and an object fitting position for the μ-probe, 8 and 9 respectively denote a pull load measuring means and deposit forming gas and 10 and 11 respectively denote a corpuscular beam and a deposit for fixing the μ-probe 6 and the thin film 2.

It is preferable from the viewpoint of smoothly and reliably evaluating the adhesiveness of a micro-part for the purpose of the present invention that the embodiment further comprises a step of observing at least the condition of the specimen 1 and/or that of the μ-probe 6.

1) The Step of Isolating the Part to be Measured of a Specimen from the Surrounding Part (Isolation Step)

Figure 1B:
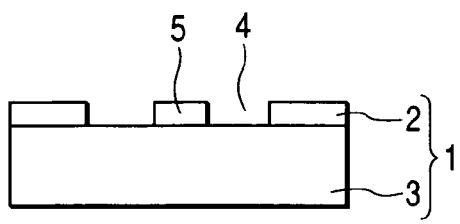

After preparing a specimen 1 as shown in FIG. 1A, the part to be measured 5 is isolated from the surrounding part 4, as shown in FIG. 1B.

While examples of specimens that can be used with this embodiment include semiconductor devices, such as memories and CPUs, imaging devices, such as CCDs and CMOSs, display devices, such as liquid crystal devices, and EL devices and micro-machines, such as angular velocity sensors and ink-jet devices, the present invention is by no means limited thereto, so long as the part to be measured can be isolated, fixed and subjected to a pull evaluation without a problem.

The specimen to be used with this embodiment may be a finished product, as mentioned above, or a product to be finished (unfinished product), such as an Si substrate to which a resist is applied, so long as the part to be measured can be isolated, fixed and subjected to a pull evaluation without a problem.

The specimen to be used with this embodiment may have any shape, and it may be film-shaped, box-shaped, spherical, cylindrical, spiral or gearwheel-shaped, so long as the part to be measured can be isolated, fixed and subjected to a pull evaluation without a problem.

When the specimen is any of various devices and micro-machines, it often takes the shape of a thin film formed on a substrate, as shown in FIG. 1A.

The surface condition of the specimen to be used with this embodiment may not necessarily be flat and smooth. The surface may be curved, undulated or stepped to a certain extent, so long as the part to be measured can be isolated, fixed and subjected to a pull evaluation without a problem.

While examples of a material of the specimen that can be used with this embodiment include metals, ceramics and organic compounds, the present invention is by no means limited thereto, so long as the part to be measured can be isolated, fixed and subjected to a pull evaluation without a problem.

The specimen to be used with this embodiment may be made of a single material or a combination of two or more than two materials, so long as the part to be measured can be isolated, fixed and subjected to a pull evaluation without a problem.

The part to be measured with this embodiment may be located on the top surface, inside, on a lateral surface or in some other area of the specimen, so long as the part to be measured can be isolated, fixed and subjected to a pull evaluation without a problem. However, if the part to be measured is located inside the specimen, the part of the specimen lying on the part to be measured may have to be removed.

The size of the part to be measured with this embodiment may be of the order of magnitude of nanometers to micrometers, for example between 10 nm and 900 μm, preferably of the order of magnitude of several tens of nanometers to several hundred micrometers, more preferably of the order of magnitude of several micrometers to several tens of micrometers.

One of the significant advantages of the present invention is that it can be used to evaluate the adhesiveness of a thin film of such a micro-region.

Examples of a technique that can be used for isolating the part to be measured include irradiation of a corpuscular beam, photolithography and mechanical scratching, although the present invention is by no means limited thereto, so long as the part to be measured can be isolated, fixed and subjected to a pull evaluation without a problem.

The part to be measured with this embodiment may be isolated by means of a single technique or a combination of two or more than two techniques, so long as the part to be measured can be isolated, fixed and subjected to a pull evaluation without a problem.

Corpuscular beams that can be used for this embodiment include an ion beam, an electron beam and a light beam. Any of such corpuscular beams may be used alone or a plurality of corpuscular beams may be combined for use, so long as the part to be measured can be isolated, fixed and subjected to a pull evaluation without a problem.

The isolation step of this embodiment is conducted preferably before the fixation step of fixing a μ-probe, which is a support member, to the part to be measured. However, alternatively, the isolation step may be conducted after the fixation step. Still alternatively, the isolation step may be conducted partly before the fixation step and the remaining part of the isolation step may be conducted after the fixation step.

However, it is preferable to conduct the isolation step before the fixation step of fixing the support member to the part to be measured for the reason described below.

When the part to be measured is isolated after fixing the support member to the part to be measured, the support member can interfere with the isolation means or the corpuscular beam being used for the isolation in the isolation step in some cases to make it difficult to isolate the part to be measured with a desired area and/or a desired shape because the support member is fixed onto the part to be measured. If the part to be measured is isolated in a state where the support member is fixed thereto, the part to be measured and/or the support member can be damaged by the excessive external force being applied from the support member to the part to be measured. If they are not damaged, the outcome of the pull evaluation can be adversely affected by the external force.

This problem can be particularly pronounced when the part to be measured has a very small size or when the part to be measured and the surrounding part have a complex shape.

2) The Step of Fixing a Support Member to the Part to be Measured (Fixation Step)

Figure 1C:
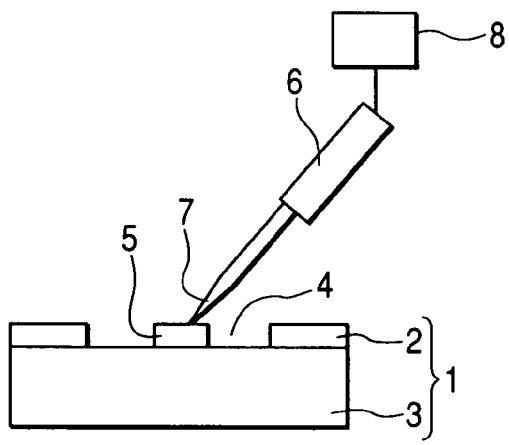
Figure 1D:
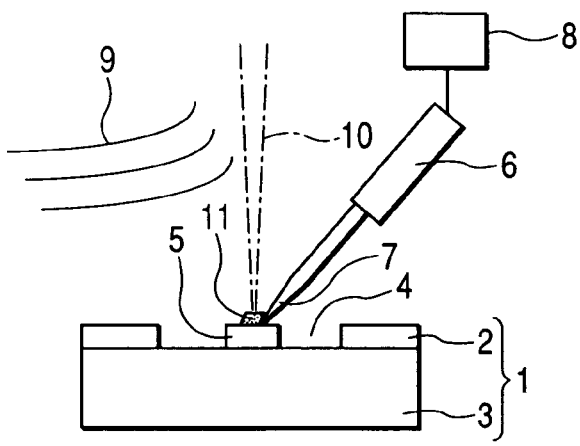

After bringing a μ-probe 6, or a support member, close to the part to be measured 5 of the specimen 1, as shown in FIG. 1C, the μ-probe 6 is fixed to the part to be measured 5 at the object fitting position 7, as shown in FIG. 1D.

While the μ-probe 6 that is used in this embodiment may have at least a position 7 where the part to be measured is fixed thereto (object fitting position), a pull load measuring means 8 or a drive mechanism for moving itself, the arrangement of the μ-probe 6 is not limited thereto, so long as the part to be measured can be isolated, fixed and subjected to a pull evaluation without a problem.

While examples of a material of the μ-probe that can be used with this embodiment include metals, ceramics and organic materials, the present invention is by no means limited thereto, so long as the part to be measured can be isolated, fixed and subjected to a pull evaluation without a problem.

The μ-probe to be used with this embodiment may be made of a single material or a combination of two or more than two materials, so long as the part to be measured can be isolated, fixed and subjected to a pull evaluation without a problem. When a piezoelectric material is used to form the μ-probe, it is possible to measure the load applied to the μ-probe by observing the applied voltage or by means of an electric instrument.

Examples of techniques that can be used for fixing the μ-probe to the part to be measured include a technique of forming a deposit and using it for the fixation, a technique of using electrostatic force for the fixation, a technique of using an adhesive for the fixation and a technique of heating the front end of the μ-probe and partly melting the part to be measured for the fixation.

However, in practical applications, the technique for fixing the μ-probe to the part to be measured is very important for the purpose of the present invention. Both the part to be measured and the μ-probe, or the support member, can have only a very limited region necessary for fixing them to each other because they intrinsically have only a very small area. Therefore, while the use of an adhesive agent may be an easy way of fixing them to each other, the area used for fixing them to each other can become greater than the micro-region to be evaluated to make it impossible to accurately evaluate the adhesiveness of the part to be measured. While a technique of heating the front end of the μ-probe and partly melting the part to be measured for fixation may be used, as described above, it can sometimes damage the part to be measured itself as a result of melting it, and consequently, alter the proper adhesiveness thereof to make it impossible to correctly carry out the pull evaluation process. While an electrostatic force can also be used for fixing the part to be measured and the μ-probe to each other, as described above, the fixing strength can sometimes be of a lower degree compared with other techniques. Sometimes, the electrostatic force cannot fix them to each other at all. On the other hand, the technique of forming a deposit and using it for the fixation (particularly, a technique of forming a deposit by irradiating a corpuscular beam to a desired spot in deposit-forming gas) is advantageous because it can avoid the above problems. Thus, this technique can suitably be used in the present embodiment.

For the purpose of the present invention, the corpuscular beam may be an ion beam, an electron beam or a light beam.

While examples of gas species that can be used for forming the deposit include organic metal compounds (e.g., $W(CO)_6$, $Mo(CO)_6$, $Ni(CO)_4$, $C_5H_5Pt(CH_3)_3$ and $Cu(hfac)_2$), organic compounds (e.g., pyrene, styrene and phenanthrene), silane compounds (e.g., TEOS and TMCTS) and metal fluorides (e.g., $WF_6$), the present invention is by no means limited thereto, so long as the part to be measured can be isolated, fixed and subjected to a pull evaluation without a problem.

Any of the above-listed gas species for forming the deposit may be used alone or in combination with some other gas, so long as the part to be measured can be isolated, fixed and subjected to a pull evaluation without a problem. For example, TEOS or TMCTS is often mixed with $O_2$ or $O_3$ for use.

3) The Step of Applying a Pulling Force to the Part to be Measured and Evaluating the Adhesiveness of the Part to be Measured (Pull Evaluation Step)

Figure 1E:
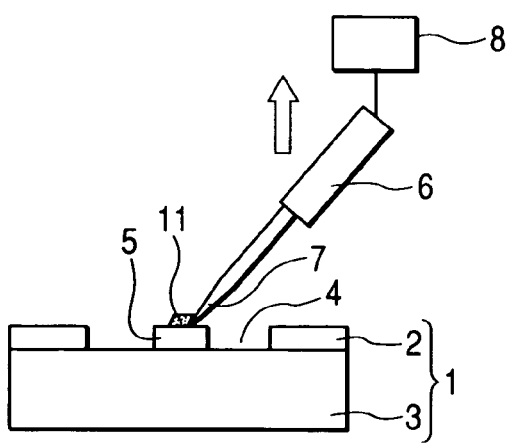
Figure 1F:
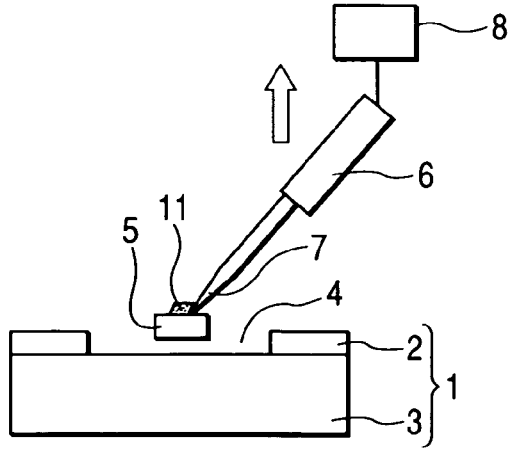

The part to be measured 5 is pulled away from the specimen 1 by applying a pulling force to the μ-probe 6 that is fixed to the part to be measured 5, as shown in FIG. 1E, to peel off the part to be measured 5, as shown in FIG. 1F, and evaluate the adhesiveness of the part to be measured 5.

While examples of techniques that can be used in this embodiment to pull the part to be measured 5 away from the specimen 1 include a technique of moving (for applying pulling force to) the μ-probe 6 that is fixed to the part to be measured 5, as shown in FIG. 1E, a technique of moving (for applying pulling force to) the specimen 1 (and the specimen stage to which the specimen is fixed) or a combination of the preceding two techniques, the present invention is by no means limited thereto, so long as the part to be measured can be isolated, fixed and subjected to a pull evaluation without a problem.

While examples of motions that can be used with this embodiment for applying a pulling force include translation in the direction of the X-axis, translation in the direction of the Y-axis, translation in the direction of the Z-axis, rotation around an appropriately defined axis and a combination of any of the preceding motions, the present invention is by no means limited thereto, so long as the part to be measured can be isolated, fixed and subjected to a pull evaluation without a problem.

Translation in the direction of the Z-axis is generally used when a flat thin film is involved, as shown in FIG. 1E. Hence, it is the direction that is most advantageous for evaluating the adhesiveness of the part to be measured. However, translation in some other direction may be used depending on the objective of evaluation, the shape of the specimen and/or some other restrictive conditions.

Because the part to be measured has a very small size, and hence, the absolute value of the pulling force necessary for peeling it off is small, it may be sometimes possible to make a pull evaluation on the part to be measured in a direction in which it is difficult to peel it off.

While examples of techniques that can be used in this embodiment for the pull evaluation include direct techniques, such as a technique of directly observing the quantity of deflection of the μ-probe and a technique of electrically measuring the quantity of deflection of the μ-probe, indirect techniques, such as a technique of determining the pulling force from the quantity of movement of the probe based on the calibration data that indicates the relationship between the quantity of movement of the probe and the pulling force and techniques of combining two or more than two of direct and indirect techniques, the present invention is by no means limited thereto, so long as the part to be measured can be isolated, fixed and subjected to a pull evaluation without a problem.

It may not be necessary to determine the absolute value of the pulling force (pulling/peeling strength) required to peel off the part to be measured depending on the object of the adhesiveness evaluation of the member (e.g., a micro-part) to be evaluated. In other words, the object of adhesiveness evaluation can be achieved in many cases by comparing the relative values of pulling/peeling strength of specimens.

Figure 2A:
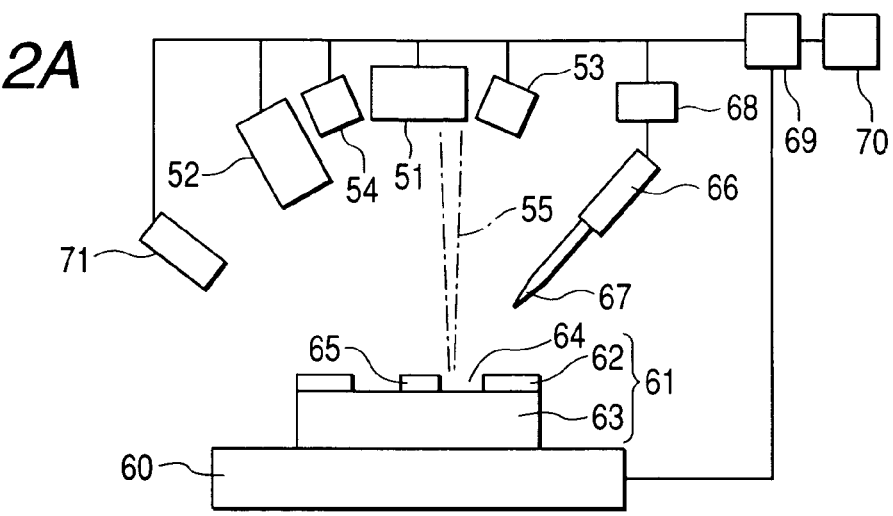
FIGS. 2A, 2B and 2C are schematic cross-sectional views of an embodiment of a micro-part adhesiveness evaluation apparatus according to the present invention.
Figure 2B:
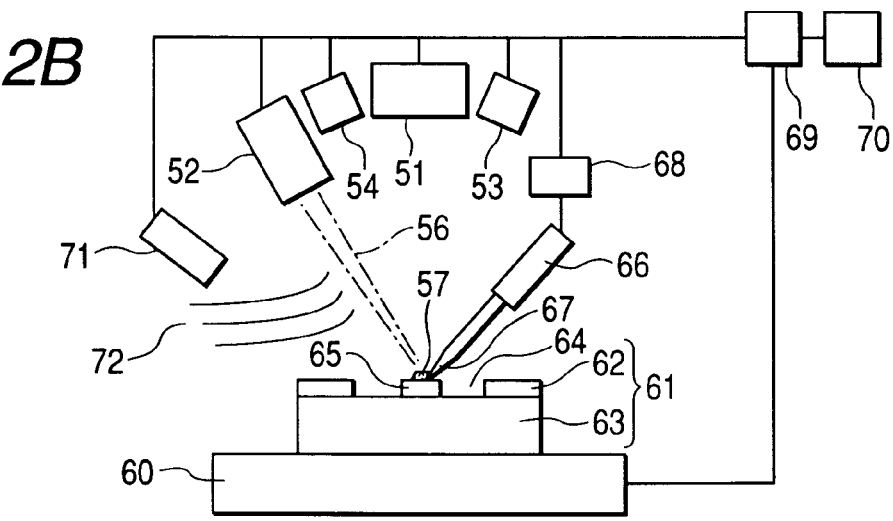
Figure 2C:
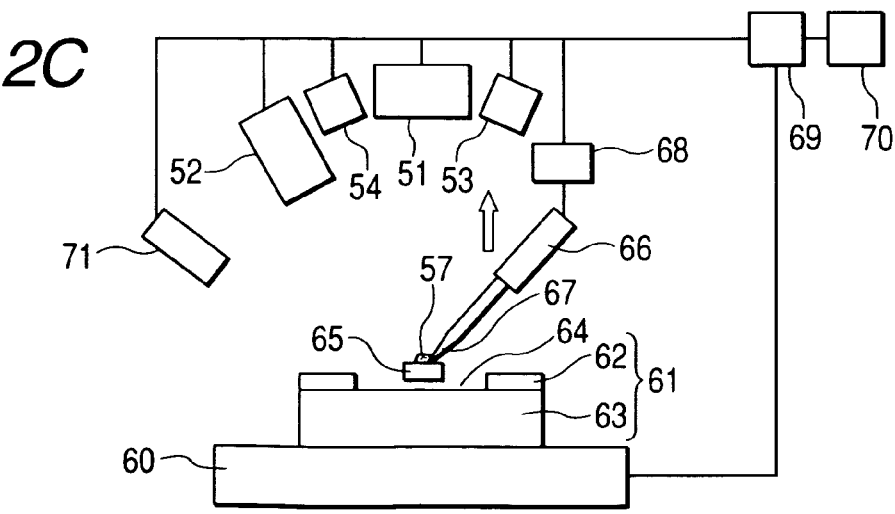

FIGS. 2A, 2B and 2C are schematic cross-sectional views of an embodiment of an apparatus for evaluating the adhesiveness according to the present invention.

The apparatus for evaluating the adhesiveness of a member in this embodiment comprises at least a means for isolating a part to be measured from a surrounding part, a means for fixing the part to be measured to a μ-probe, which is a support member, and a means for applying a pulling force to the part to be measured and evaluating the adhesiveness thereof.

From the viewpoint of smoothly and reliably evaluating the adhesiveness of a micro-part, preferably, the apparatus for evaluating the adhesiveness of a micro-part of this embodiment further comprises a means for observing at least the condition of the specimen 1 and/or that of the μ-probe, which is a support member, by means of a corpuscular beam III.

Referring to FIGS. 2A through 2C, reference numerals 51, 52, 53, 54, 55, 56 and 57 respectively denote an irradiation system of corpuscular beam I, an irradiation system of corpuscular beam II, a detection system of the signal generated when the corpuscular beam I is irradiated, a detection system of the signal generated when the corpuscular beam II is irradiated, the corpuscular beam I, the corpuscular beam II and a deposit for fixing, while reference numerals 60, 61, 62, 63, 64, 65, 66, 67, 68, 69, 70, 71 and 72 respectively denote a specimen stage, a specimen including a first member and a second member, a thin film of the second member, a substrate of the first member, a surrounding part, a part to be measured isolated from the surrounding part 64, a μ-probe that is a support member, an object-fitting position of the μ-probe, a pull evaluation means, a control system, an observation/display system, a deposit-forming gas-introducing system and deposit-forming gas.

The above-listed components are arranged in a vacuum container (not shown), if necessary, which vacuum container is evacuated by a vacuuming/exhausting system (not shown). Additionally, the control system 69 controls the adhesiveness evaluation apparatus by exchanging signals with the irradiation system 51 of corpuscular beam I, the irradiation system 52 of corpuscular beam II, the detection system 53 of the signal generated when the corpuscular beam I is irradiated, the detection system 54 of the signal generated when the corpuscular beam II is irradiated, the specimen stage 60, the μ-probe 66, the pull evaluation means of the μ-probe 68, the observation/display system 60, the deposit-forming gas-introducing system 71 and a vacuum control system (not shown).

It is possible to confirm the position for irradiating corpuscular beam I 55 at the observation/display system 70 by controlling the irradiation system 51 so as to irradiate the corpuscular beam I 55 and using the detection system 53 of the signal generated when the corpuscular beam I 55 is irradiated.

Similarly, it is possible to confirm the position for irradiating corpuscular beam II 56 at the observation/display system 70 by controlling the irradiation system 52 so as to irradiate the corpuscular beam II 56 and using the detection system 54 of the signal generated when the corpuscular beam II 56 is irradiated.

The specimen stage 60 carries the specimen 61 on it, so that it is possible to move the specimen 61 with the specimen stage 60 by controlling the specimen stage 60.

The μ-probe 66 has at least the object-fitting position 67 of the μ-probe, the pull evaluation means 68 and a μ-probe drive section (not shown). The pulling force is measured by controlling the pull evaluation means 68 and the μ-probe is moved by controlling the μ-probe drive section.

Deposit-forming gas 72 is introduced by controlling the deposit forming gas-introducing system 71. It is possible to selectively form the deposit 57 for fixing the part to be measured to a desired position by irradiating the corpuscular beam II 56 to the desired position while introducing the deposit-forming gas 72 (FIG. 2B).

The adhesiveness evaluation method using the adhesiveness evaluation apparatus of this embodiment is described blow.

(a) Isolation of the Part to be Measured of the Specimen from the Surrounding Part The part to be measured 65 of the specimen 61 is isolated from the surrounding part 64, as shown in FIG. 2A.

Examples of a technique of this embodiment that can be used for isolating the part to be measured include irradiation of a corpuscular beam, photolithography and mechanical scratching, although the present invention is by no means limited thereto, so long as the part to be measured can be isolated, fixed and subjected to a pull evaluation without a problem. The part to be measured with this embodiment may be isolated by means of a single technique or a combination of two or more than two techniques, so long as the part to be measured can be isolated, fixed and subjected to a pull evaluation without a problem.

Corpuscular beams that can be used for this embodiment include an ion beam, an electron beam and a light beam. Any of such corpuscular beams may be used alone or a plurality of corpuscular beams may be combined for use, so long as the part to be measured can be isolated, fixed and subjected to a pull evaluation without a problem.

The isolation step of this embodiment is conducted preferably before the fixation step of fixing a μ-probe, which is a support member, to the part to be measured. However, alternatively, the isolation step may be conducted after the fixation step. Still alternatively, the isolation step may be conducted partly before the fixation step, and the remaining part of the isolation step may be conducted after the fixation step. However, the present invention is by no means limited thereto, so long as the part to be measured can be isolated, fixed and subjected to a pull evaluation without a problem.

Nonetheless, it is preferable to conduct the isolation step before the fixation step of fixing the support member to the part to be measured for the reason described below.

When the part to be measured is isolated after fixing the support member to the part to be measured, the support member can interfere with the isolation means or the corpuscular beam being used for the isolation in the isolation step in some cases to make it difficult to isolate the part to be measured with a desired area and/or a desired shape because the support member is fixed onto the part to be measured. If the part to be measured is isolated in a state where the support member is fixed thereto, the part to be measured and/or the support member can be damaged by the excessive external force being applied from the support member to the part to be measured. If they are not damaged, the outcome of the pull evaluation can be adversely affected by the external force.

This problem can be particularly pronounced when the part to be measured has a very small size or when the part to be measured and the surrounding part have a complex shape.

While examples of specimens in this embodiment include semiconductor devices, such as memory units and CPUs, imaging devices, such as CCDs and CMOSs, display devices, such as liquid crystal devices and EL devices, and micro-machines, such as angular velocity sensors and ink-jet devices, the present invention is by no means limited thereto, so long as the part to be measured can be isolated, fixed and subjected to a pull evaluation without a problem.

The specimen in this embodiment may be a finished product, as mentioned above, or a product to be finished (unfinished product), such as an Si substrate to which resist is applied, so long as the part to be measured can be isolated, fixed and subjected to a pull evaluation without a problem.

The specimen in this embodiment may have any shape, and may be film-shaped, box-shaped, spherical, cylindrical, spiral or gearwheel-shaped, so long as the part to be measured can be isolated, fixed and subjected to a pull evaluation without a problem. When the specimen is any of various devices and micro-machines, it often takes the shape of a thin film formed on a substrate, as shown in FIG. 1A.

The surface condition of the specimen to be used with this embodiment may not necessarily be flat and smooth. The surface may be curved, undulated or stepped to a certain extent, so long as the part to be measured can be isolated, fixed and subjected to a pull evaluation without a problem.

While examples of the material of the specimen that can be used in this embodiment include metals, ceramics and organic compounds, the present invention is by no means limited thereto, so long as the part to be measured can be isolated, fixed and subjected to a pull evaluation without a problem. The specimen to be used in this embodiment may be made of a single material or a combination of two or more than two materials, so long as the part to be measured can be isolated, fixed and subjected to a pull evaluation without a problem.

The part to be measured in this embodiment may be located on the top surface, inside, on a lateral surface or in some other area of the specimen, so long as the part to be measured can be isolated, fixed and subjected to a pull evaluation without a problem. However, if the part to be measured is located inside the specimen, the part of the specimen lying on the part to be measured may have to be removed.

The size of the part to be measured in this embodiment is of the order of magnitude of micrometers, preferably of the order of magnitude of several tens of nanometers to several hundred micrometers, more preferably of the order of magnitude of several micrometers to several tens of micrometers.

One of the significant advantages of the present invention is that it can be used to evaluate the adhesiveness of a thin film of such a micro-region.

(b) Fixation of the Part to be Measured to the Support Member

The μ-probe 66 is fixed to the part to be measured 65 at the object fitting position 67 in a state where the μ-probe 66, or a support member, is placed close to the part to be measured 65 of the specimen 61, as shown in FIG. 2B.

While examples of techniques that can be used for fixing the μ-probe to the part to be measured include a technique of forming a deposit and using it for the fixation, a technique of using electrostatic force for the fixation, a technique of using an adhesive for the fixation and a technique of heating the front end of the μ-probe and partly melting the part to be measured for the fixation, this embodiment is by no means limited thereto, so long as the part to be measured can be isolated, fixed and subjected to a pull evaluation without a problem.

However, in practical applications, the technique for fixing the μ-probe to the part to be measured is very important for the purpose of the present invention. Both the part to be measured and the μ-probe, or the support member, can have only a very limited region necessary for fixing them to each other because these parts intrinsically have only a very small area (of the order of magnitude of micrometers). Therefore, while the use of an adhesive agent may be an easy way of fixing the part to be measured and the μ-probe, or the support member to each other, the area used for fixing can become greater than the micro-region to be evaluated to make it impossible to accurately evaluate the adhesiveness of the part to be measured. While a technique of heating the front end of the μ-probe and partly melting the part to be measured for fixation can be used, as described above, it can sometimes damage the part to be measured itself as a result of melting it, and consequently, alter the proper adhesiveness thereof to make it impossible to correctly carry out the pull evaluation process. While an electrostatic force can also be used, as described above, it can sometimes fix the part to be measured and the μ-probe to each other only with a lower degree of fixing strength compared with other techniques, and sometimes, it cannot fix them to each other at all. On the other hand, the technique of forming a deposit and using it for the fixation (particularly, a technique of forming a deposit by irradiating a corpuscular beam to a desired spot in deposit-forming gas) is advantageous because it can avoid the above problems. Thus, this technique is one of the techniques that can suitably be used in the present embodiment. For the purpose of the present invention, the corpuscular beam may be an ion beam, an electron beam or a light beam.

While examples of the gas species that can be used for forming the deposit include organic metal compounds (e.g., $W(CO)_6$, $Mo(CO)_6$, $Ni(CO)_4$, $C_5H_5Pt(CH_3)_3$ and $Cu(hfac)_2$), organic compounds (e.g., pyrene, styrene and phenanthrene), silane compounds (e.g., TEOS and TMCTS) and metal fluorides (e.g., $WF_6$), the present invention is by no means limited thereto, so long as the part to be measured can be isolated, fixed and subjected to a pull evaluation without a problem.

Any of the above-listed gas species for forming the deposit may be used alone or in combination with some other gas, so long as the part to be measured can be isolated, fixed and subjected to a pull evaluation without a problem. For example, TEOS or TMCTS is often mixed with $O_2$ or $O_3$ for use.

While the μ-probe that is used in this embodiment may have at least a position where the part to be measured is fixed thereto (object fitting position), a pull load measuring means or a drive mechanism for moving itself, the arrangement of the μ-probe is not limited thereto, so long as the part to be measured can be isolated, fixed and subjected to a pull evaluation without a problem.

While examples of the material of the μ-probe that can be used in this embodiment include metals, ceramics and organic materials, the present invention is by no means limited thereto, so long as the part to be measured can be isolated, fixed and subjected to a pull evaluation without a problem.

The μ-probe to be used win this embodiment may be made of a single material or a combination of two or more than two materials, so long as the part to be measured can be isolated, fixed and subjected to a pull evaluation without a problem. When a piezoelectric material is used to form the μ-probe, it is possible to measure the load applied to the μ-probe by observing the applied voltage or by means of an electric instrument.

(c) Evaluation of Adhesiveness by Applying a Pulling Force to the Part to be Measured The part to be measured 65 is pulled away from the specimen 61 by applying a pulling force to this part, as shown in FIG. 2C, to peel off the part to be measured 65 and evaluate the adhesiveness of the part to be measured.

While examples of techniques that can be used in this embodiment to pull the part to be measured 65 away from the specimen 61 include a technique of moving (for applying pulling force to) the μ-probe 66 that is fixed to the part to be measured 65, as shown in FIG. 2C, a technique of moving (for applying pulling force to) the specimen 61 (and the specimen stage 60 to which the specimen is fixed) or a combination of the preceding two techniques, the present invention is by no means limited thereto, so long as the part to be measured can be isolated, fixed and subjected to a pull evaluation without a problem.

While examples of motions that can be used with this embodiment for applying pulling force include translation in the direction of the X-axis, translation in the direction of the Y-axis, translation in the direction of the Z-axis, rotation around an appropriately defined axis and a combination of any of the preceding motions, the present invention is by no means limited thereto, so long as the part to be measured can be isolated, fixed and subjected to a pull evaluation without a problem.

Translation in the direction of the Z-axis is generally used when a flat thin film is involved, as shown in FIG. 2C. Hence, it is the direction that is most advantageous for evaluating the adhesiveness of the part to be measured. However, translation in some other direction may be used depending on the objective of the evaluation, the shape of the specimen and/or some other restrictive conditions. Because the part to be measured has a very small size, and hence, the absolute value of the pulling force necessary to peel it off is small, it may be sometimes possible to make a pull evaluation on the part to be measured in a direction in which it is difficult to peel it off.

While examples of techniques that can be used in this embodiment for the pull evaluation include direct techniques, such as a technique of directly observing the quantity of deflection of the μ-probe and a technique of electrically measuring the quantity of deflection of the μ-probe, indirect techniques, such as a technique of determining the pulling force from the quantity of movement of the probe based on the calibration data that indicates the relationship between the quantity of movement of the probe and the pulling force, and techniques of combining two or more than two of direct and indirect techniques, the present invention is by no means limited thereto, so long as the part to be measured can be isolated, fixed and subjected to a pull evaluation without a problem.

It may not be necessary to determine the absolute value of the pulling force (pulling/peeling strength) required to peel off the part to be measured depending on the object of adhesiveness evaluation of the micro-part. In other words, the object of the adhesiveness evaluation can be achieved in many cases by comparing the relative values of the pulling/peeling strength of specimens.

In this embodiment, the corpuscular beam I is irradiated at the time of isolating the part to be measured and the corpuscular beam II is irradiated at the time of forming the deposit for the purpose of fixation, whereas the corpuscular beam III is irradiated at the time of conducting the observation. All or two of the corpuscular beams I, II and III may be identical to each other or all the corpuscular beams I, II and III may be different from each other, so long as the part to be measured can be isolated, fixed and subjected to a pull evaluation without a problem.

Accordingly, all or two of the corpuscular beam irradiation systems for irradiating the corpuscular beams I, II and III may be identical to each other or all the corpuscular beam irradiation systems may be different from each other, so long as the part to be measured can be isolated, fixed and subjected to a pull evaluation without a problem. It is not necessary to provide the irradiation system for irradiating the corpuscular beam I in a system where the part to be measured does not need to be isolated.

Each of the corpuscular beam irradiation systems for irradiating the corpuscular beams I, II and III may be a single system or a multi-system, so long as the part to be measured can be isolated, fixed and subjected to a pull evaluation without a problem.

While examples of techniques for irradiating a corpuscular beam that can be used in this embodiment include a technique of irradiating a converged corpuscular beam while scanning it in a desired region, a technique of irradiating a corpuscular beam that is diverging to a certain extent while scanning it in a desired region and a combination of the preceding techniques, this embodiment is by no means limited thereto, so long as the part to be measured can be isolated, fixed and subjected to a pull evaluation without a problem.

Corpuscular beams that can be used in this embodiment include an ion beam, an electron beam and a light beam. However, this embodiment is by no means limited thereto, so long as the part to be measured can be isolated, fixed and subjected to a pull evaluation without a problem.

Any of such corpuscular beams may be used alone or a plurality of corpuscular beams may be combined for use, so long as the part to be measured can be isolated, fixed and subjected to a pull evaluation without a problem.

Further, when a plurality of corpuscular beams are combined for use, corpuscular beams may be used simultaneously, used in turn or combined. However, this embodiment is by no means limited thereto, so long as the part to be measured can be isolated, fixed and subjected to a pull evaluation without a problem.

When the corpuscular beams in this embodiment are ion beams, ion species that can be used for the ion beams include Ga, Si, Ge, Cs, Nb and Cu that are liquid metal ion sources and O, N, H, He and Ar that are field ionization gas ion sources, although an ion species that can be used for this embodiment is by no means limited thereto, so long as the part to be measured can be isolated, fixed and subjected to a pull evaluation without a problem.

However, in practical applications, Ga is often used as the ion species of the ion beams because of the ease of handling.

When the corpuscular beams of this embodiment are electron beams, techniques for forming electrons that can be used for this embodiment include one for emitting thermal electrons, one using field emission, one for emitting electrons by a tunnel effect and one for emitting photoelectrons, although this embodiment is by no means limited thereto, so long as the part to be measured can be isolated, fixed and subjected to a pull evaluation without a problem.

When the corpuscular beams of this embodiment are light beams, the light beams may be selected from X-rays, ultraviolet rays, rays of visible light and infrared rays, although this embodiment is by no means limited thereto, so long as the part to be measured can be isolated, fixed and subjected to a pull evaluation without a problem. Additionally, laser beams are often used because of the ease of handling they provide.

EXAMPLES

The above embodiments are described below in greater detail by way of Examples.

Example 1

In this Example, the adhesiveness of a thin film formed on a substrate is evaluated by means of the micro-part adhesiveness evaluation method of the above embodiment, as will be described below, by referring to FIGS. 1A through 1F.

Although not described below explicitly, this Example includes a step of observing the condition of the specimen 1 and that of the µ-probe 6 by detecting secondary electrons that are generated when an electron beam is irradiated for scanning (by means of an SEM: scanning electron microscopy).

1) The Step of Isolating the Part of a Specimen to be Measured from the Surrounding Part (Isolation Step)

A thin film 2 is prepared on a substrate 3 as specimen 1, as shown in FIG. 1A. Then, an ion beam 10 is irradiated onto the surrounding part 4 of the part to be measured 5 of the specimen 1 in order to isolate the part to be measured 5 from the surrounding part 4 by etching. The size of the part to be measured is about 7×7 µm.

2) The Step of Fixing a Support Member to the Part of the Second Member to be Measured (Fixation Step)

A µ-probe 6, which is a support member, is brought close to the part to be measured 5 of the specimen 1, as shown in FIG. 1C. The µ-probe 6 is fixed to the part to be measured 5 by irradiating an ion beam 10 onto the object fitting position 7 of the µ-probe 6 in tungsten carbonyl gas 9 in a state where the part to be measured 5 and the µ-probe 6 are brought close to each other so as to form a deposit 11 of tungsten on the part to be measured 5 and cover the front end of the µ-probe 6, as shown in FIG. 1D.

3) The Step of Applying a Pulling Force to the Part to be Measured and Evaluating the Adhesiveness of the Part to be Measured (Pull Evaluation Step)

The µ-probe 6 fixed to the part to be measured 5 is moved in the Z-direction to apply a pulling force to the part to be measured 5, as shown in FIG. 1E. The part to be measured 5 is peeled off from the substrate 3 of the specimen 1 when the pulling force exceeds a certain level, as shown in FIG. 1F. The pulling force is determined by a pull evaluation means at this time. Note that the pulling force is determined here from the quantity of movement of the probe from the calibration data that indicates the relationship between the quantity of movement of the probe and the pulling force.

As pointed out above, it is possible to select a specific spot (of the order of magnitude of nanometers to micrometers) of a micro-part of the specimen and evaluate the adhesiveness of the spot.

Example 2

The above embodiment of apparatus for evaluating the adhesiveness of a micro-part will be described in this Example by referring to FIGS. 2A through 2C.

The components of this embodiment are arranged in a vacuum container (not shown), if necessary, which vacuum container is evacuated by a vacuuming/exhausting system (not shown). Additionally, the control system 69 controls and operates the micro-part adhesiveness evaluation apparatus by exchanging signals with the irradiation system 51 of ion beam, the irradiation system 52 of electron beam, the detection system 53 of the signal generated when the ion beam is irradiated, the detection system 54 of the signal generated when the electron beam is irradiated, the specimen stage 60, the y-probe 66, the pull evaluation means of the µ-probe 68, the observation/display system 70, the deposit-forming gas-introducing system 71 and a vacuum control system (not shown).

It is possible to confirm the position for irradiating ion beam 55 at the observation/display system 70 by controlling the irradiation system 51 so as to irradiate the ion beam 55 and using the detection system 53 of the signal generated when the ion beam 55 is irradiated. Similarly, it is possible to confirm the position for irradiating electron beam 56 at the observation/display system 70 by controlling the irradiation system 52 so as to irradiate the electron beam 56 and using the detection system 54 of the signal generated when the electron beam 56 is irradiated.

The specimen stage 60 carries the specimen 61 on it so that it is possible to move the specimen 61 with the specimen stage 60 by controlling the specimen stage 60.

The µ-probe 66 has at least the object-fitting position 67, the pull evaluation means 68 and a µ-probe drive section (not shown). The pulling force is measured by controlling the pull evaluation means 68, and the µ-probe is moved by controlling the µ-probe drive section.

Deposit forming gas 72, which is pyrene gas, is introduced by controlling the deposit forming gas introducing system 71. It is possible to selectively form the deposit 57 (which contains carbon as a principal ingredient) for fixing the part to be measured to a desired position by irradiating the ion beam 55 or the electron beam 56 to the desired position while introducing pyrene gas 72 (FIG. 2B).

Furthermore, it is possible to appropriately observe the condition of the specimen 61 and that of the y-probe 66 by means of the detection system 54 for detecting secondary electrons that are generated when the electron beam 56 is irradiated for scanning (by means of an SEM: scanning electron microscopy).

Evaluation

It is possible to carry out an operation similar to that in Example 1 by means of the micro-part adhesiveness evaluation apparatus of this embodiment.

Thus, it is possible to evaluate the adhesiveness of the part to be measured of the second member that constitutes the object of measurement to the first member by applying a pulling force to the second member by way of the support member fixed to the second member using this embodiment.

When a μ-probe is used for the support member, it is possible to evaluate the adhesiveness of a micro-part of the specimen. Also, it is possible to evaluate the adhesiveness of a specific spot of the micro-part of the specimen because any desired spot can be selected in the isolation step. Additionally, it is possible to select a desired size for the part to be measured in the isolation step. Therefore, it is possible to increase the accuracy of the evaluation of the adhesiveness of the micro-part by increasing the degree of freedom of the evaluation.

Since a corpuscular beam is used in the isolation step of this embodiment, it is possible to avoid any application of an external force (physical energy) that can adversely affect the outcome of the pull evaluation compared with an arrangement of cutting the thin film formed on a substrate to produce a checker pattern, as described above in connection with the related background art.

Additionally, where a deposit is formed in the fixation step of fixing the support member to the part to be measured in this embodiment, it is possible to avoid any application of an external force (thermal energy) that can adversely affect the outcome of the pull evaluation compared with an arrangement of fixing the support member by heating and melting the thin film formed on a substrate.

Finally, it is possible to carry out the isolation step, the fixation step and the pull evaluation step of this embodiment of the present invention easily within a same apparatus in a short period of time.

This application claims priority from Japanese Patent Application Nos. 2004-171305, filed on Jun. 6, 2004 and 2005-144069, filed on May 17, 2005, which are hereby incorporated by reference herein.

What is claimed is:

1. A method of evaluating adhesiveness of a first member to a second member, which is arranged on the first member, comprising at least:
   a preparation step of preparing a specimen for measurement including the first member and the second member arranged on the first member;
   an isolation step of isolating a part to be measured of the second member from a surrounding part, the part to be measured having a size between 10 nm and 900 μm;
   a fixation step of fixing a support member to the part to be measured of the second member after the isolation step; and
   an evaluation step of applying a pulling force to the part to be measured of the second member by way of the support member and evaluating the adhesiveness between the first member and the part to be measured of the second member by peeling off the part to be measured of the second member from the first member, wherein said isolation step is conducted by using an ion beam, an electron beam or a light beam.

2. The method according to claim 1, wherein said fixing step is conducted by depositing a substance and fixing said support member to said part to be measured of said second member.

3. The method according to claim 2, wherein said fixing step includes irradiation of one or more than one of an ion beam, an electron beam or a light beam in a gas atmosphere for forming a deposit of a substance.

4. The method according to claim 1, wherein said evaluation step includes a step of pulling said support member or moving a stage holding said specimen.

5. The method according to claim 1, wherein said second member is a thin film.

6. A method of evaluating adhesiveness of a first member to a second member, which is arranged on the first member, comprising at least:
   a step of preparing a specimen for measurement including the first member and the second member arranged on the first member;
   a step of arranging a support member to a part to be measured of the second member, the part to be measured having a size between 10 nm and 900 μm;
   a step of depositing a substance on the part to be measured of the second member carrying the support member arranged thereto and fixing the support member to the part to be measured of the second member; and
   a step of applying a pulling force to the part to be measured of the second member by way of the support member and evaluating the adhesiveness between the first member and the part to be measured of the second member by peeling off the part to be measured of the second member from the first member, wherein said fixing substance is deposited by irradiating one or more than one of an ion beam, an electron beam or a light beam in a gas atmosphere for forming a deposit of a substance.

7. The method according to claim 6, wherein said second member is a thin film.

* * * * *